US012636121B2

(12) United States Patent
Murdeshwar et al.

(10) Patent No.: US 12,636,121 B2
(45) Date of Patent: May 26, 2026

(54) WEARABLE SUPPORT STRUCTURES FOR MEDICAL DEVICES

(71) Applicant: OLYMPUS MEDICAL SYSTEMS CORP., Tokyo (JP)

(72) Inventors: Nikhil M. Murdeshwar, Maple Grove, MN (US); Kester Julian Batchelor, Mound, MN (US)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 815 days.

(21) Appl. No.: 17/933,622

(22) Filed: Sep. 20, 2022

(65) Prior Publication Data

US 2023/0095909 A1     Mar. 30, 2023

Related U.S. Application Data

(60) Provisional application No. 63/261,705, filed on Sep. 27, 2021.

(51) Int. Cl.
| | |
|---|---|
| *A61B 90/60* | (2016.01) |
| *A61B 34/00* | (2016.01) |
| *A61G 13/12* | (2006.01) |

(52) U.S. Cl.
CPC .............. *A61B 90/60* (2016.02); *A61B 34/74* (2016.02); *A61G 13/1235* (2013.01)

(58) Field of Classification Search
CPC ......... A61B 90/60; A61B 34/74; A61B 90/57; A61B 90/53; A47B 21/0371; A61G 7/1053; A61F 5/3746; A61F 5/3723; A61F 5/05858; A61F 5/0118; B25J 9/0006; F16M 13/04; F16M 13/022; G05G 7/02

See application file for complete search history.

(56) References Cited

U.S. PATENT DOCUMENTS

| | | | |
|---|---|---|---|
| 2,594,809 | A | 4/1952 | Sanders |
| 2,875,754 | A | 3/1959 | Messer |
| 4,420,149 | A | 12/1983 | Schultes et al. |

(Continued)

FOREIGN PATENT DOCUMENTS

| | | |
|---|---|---|
| JP | 2016016157 A | 2/2016 |

*Primary Examiner* — Matthew Troutman
*Assistant Examiner* — Alison N Labarge
(74) *Attorney, Agent, or Firm* — Schwegman Lundberg & Woessner, P.A.

(57)     ABSTRACT

A system for supporting a surgical instrument relative to a body of a user can comprise a body-mountable portion for supporting an arm of the user, the body-mountable portion comprising a forearm support, an instrument support connected to the body-mountable portion to hold a handle of the surgical instrument proximate the forearm support, and a positioning device configured to hold a position of the instrument support relative to the body-mountable portion. A method for supporting a medical instrument against the body of a user can comprise placing an arm of the user in a support structure, attaching the support structure to the body, positioning the medical instrument in an instrument support connected to the support structure, and adjusting a positioning device to fix a position of the medical instrument relative to the body. In examples, the support structure can comprise an exoskeleton sleeve.

18 Claims, 6 Drawing Sheets

(56)         References Cited

U.S. PATENT DOCUMENTS

| | | | | |
|---|---|---|---|---|
| 5,086,762 | A * | 2/1992 | Chee | A47B 21/0371 |
| | | | | 400/715 |
| 6,971,987 | B1 | 12/2005 | Chung | |
| 7,731,652 | B2 | 6/2010 | Surti et al. | |
| 8,029,452 | B2 * | 10/2011 | Kliewer | A61B 8/4227 |
| | | | | 403/114 |
| 9,205,017 | B2 * | 12/2015 | Doyle | A61F 5/013 |
| 9,931,701 | B1 * | 4/2018 | Klein | B25F 5/026 |
| 2006/0259018 | A1 * | 11/2006 | Shilkrut | F16M 13/022 |
| | | | | 606/1 |
| 2009/0192511 | A1 * | 7/2009 | Haffenreffer | A61B 17/02 |
| | | | | 606/53 |
| 2012/0184880 | A1 * | 7/2012 | Doyle | B25J 9/0006 |
| | | | | 601/33 |
| 2012/0197075 | A1 | 8/2012 | Krimsky et al. | |
| 2014/0033391 | A1 * | 2/2014 | Doyle | A61B 90/53 |
| | | | | 2/16 |
| 2014/0158839 | A1 * | 6/2014 | Doyle | A61F 5/013 |
| | | | | 248/118 |
| 2016/0303734 | A1 * | 10/2016 | Bowles | A61B 17/2909 |
| 2018/0055591 | A1 * | 3/2018 | Bonny | A61B 90/57 |
| 2018/0295998 | A1 * | 10/2018 | Barnes | B25J 9/0006 |
| 2019/0249825 | A1 * | 8/2019 | Doyle | F16M 13/04 |

* cited by examiner

WEARABLE SUPPORT STRUCTURES FOR MEDICAL DEVICES

CLAIM FOR PRIORITY

This application claims the benefit of priority of U.S. Application Ser. No. 63/261,705, filed Sep. 27, 2021, which is hereby incorporated by reference in its entirety.

TECHNICAL FIELD

The present disclosure relates generally, but not by way of limitation, to medical instruments and devices, such as those comprising elongate bodies configured to be inserted into incisions or openings in anatomy of a patient to provide diagnostic or treatment operations, such as by cutting, cauterizing or collecting tissue with a forceps.

More specifically, the present disclosure relates to structures that can be used to provide support to a user or operator of medical devices, such as endoscopes, laparoscopes and other surgical instruments, in order to enhance comfort and performance of the user and reduce fatigue.

BACKGROUND

Endoscopes can be used for one or more of 1) providing passage of other devices, e.g., therapeutic devices or tissue collection devices, toward various anatomical portions of a patient, and 2) imaging of such anatomical portions. Such anatomical portions can include the gastrointestinal tract (e.g., esophagus, stomach, duodenum, pancreaticobiliary duct, intestines, colon, etc.), renal area (e.g., kidney(s), ureter, bladder, urethra, etc.), other internal organs (e.g., reproductive systems, sinus cavities, submucosal regions, respiratory tract), and the like.

Conventional endoscopes can be involved in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices for sampling or treating an anatomical region, and providing suction passageways for collecting fluids (e.g., saline or other preparations), and the like.

In view of the foregoing, medical procedures using scopes can involve time and skill to deliver the device to the desired target anatomy where the device is to be used to perform the diagnosis and treatment. Use of such scopes can involve holding the handle of the scope close to the user to facilitate ease of use, while also maintaining close proximity to the patient and a control system. Additionally, the user typically tries to prevent portions of the device, such as cords, tubes and the like, from touching the floor or portions of the patient not involved in the procedure. Furthermore, manipulation of control elements on the handle is simultaneously conducted with the same arm supporting the weight of the handle. Thus, such procedures can require the user to hold the instrument in a single position for a long period of time, which can cause strain and fatigue.

Examples of structures that have been developed in attempts to alleviate user arm fatigue are described in U.S. Pat. No. 7,731,652 B2 to Surti et al.; Pub. No. JP 2016-16157 A to Ishii et al.; U.S. Pat. No. 6,971,987 B1 to Chung; and Pub. No. US 2012/0197075 A1 to Krimsky et al.

SUMMARY

The present inventors have recognized that problems to be solved with medical instruments, and in particular medical scopes, such as endoscopes and laparoscopes, used to treat and retrieve biological matter or perform other procedures, can include, among other things, muscle strain and fatigue of the user. Furthermore, the present inventors have recognized that structures developed in attempts to alleviate this muscle strain and fatigue can sometimes 1) be difficult to put on, 2) be overly restrictive when worn, 3) lock the medical instrument into only a single position, and 4) limit use of the arm supported by such device to performing a limited number of tasks. The present inventors have also recognized that these problems exist in endoscopic retrograde cholangiopancreatography (ERCP) procedures where a duodenoscope is used in conjunction with an auxiliary scope. In an ERCP procedure, the auxiliary scope (also referred to as daughter scope, or cholangioscope) can be attached and advanced through the working channel of the duodenoscope (also referred to as a mother scope or "main scope"). Furthermore, a tissue retrieval device used to remove sample matter can be inserted through the auxiliary scope. As such, the duodenoscope, auxiliary scope and tissue retrieval device become progressively smaller, due to being sequentially inserted in progressively smaller lumens, and more difficult to maneuver and perform interventions and treatments. Additionally, the surgeon is frequently required to operate three different controllers for these three different devices, often at the same time. Thus, operation of controls for three different instruments further produces the opportunity for muscle strain and fatigue.

The present disclosure can help provide solutions to these and other problems by providing systems, devices and methods relating to structures for supporting medical instruments for a user in order to reduce or eliminate strain and fatigue during use. Such structures can comprise slings, vests and exoskeletons into which an arm a user can be inserted and to which a medical instrument can be mounted in, for example, an adjustable mount. The slings, vests and exoskeletons can allow the arm to be removed intraoperatively while the instrument is held in place. The adjustable mount can allow the medical instrument to be put into a user-selected position that is both ergonomic and functional. The adjustable mount can additionally automate functions of the medical instrument to alleviate the need for the user to actuate or hold control elements, e.g., buttons and knobs, of the medical instrument. The adjustable mount can further include multiple sockets or receptacle to hold multiple medical instruments, such as control handles for a duodenoscope and a cholangioscope.

In an example, a system for supporting a surgical instrument relative to a body of a user can comprise a body-mountable portion for supporting an arm of the user, the body-mountable portion comprising a forearm support, an instrument support connected to the body-mountable portion to hold a handle of the surgical instrument proximate the forearm support, and a positioning device configured to hold a position of the instrument support relative to the body-mountable portion.

In another example, a structure for supporting a medical instrument for a user can comprise a support base defining a stationary structure, an exoskeleton connected to the support base that can comprise a humeral support extending form the support base, an elbow pivot joint connected to the humeral support, and an ulnar support extending from the elbow pivot joint, a locking mechanism for the elbow pivot joint, and a device support connected to the ulnar support.

In an example, a method for supporting a medical instrument against the body of a user can comprise placing an arm of the user in a support structure, attaching the support structure to the body, positioning the medical instrument in an instrument support connected to the support structure, and adjusting a positioning device to fix a position of the medical instrument relative to the body.

DETAILED DESCRIPTION

Figure 1:
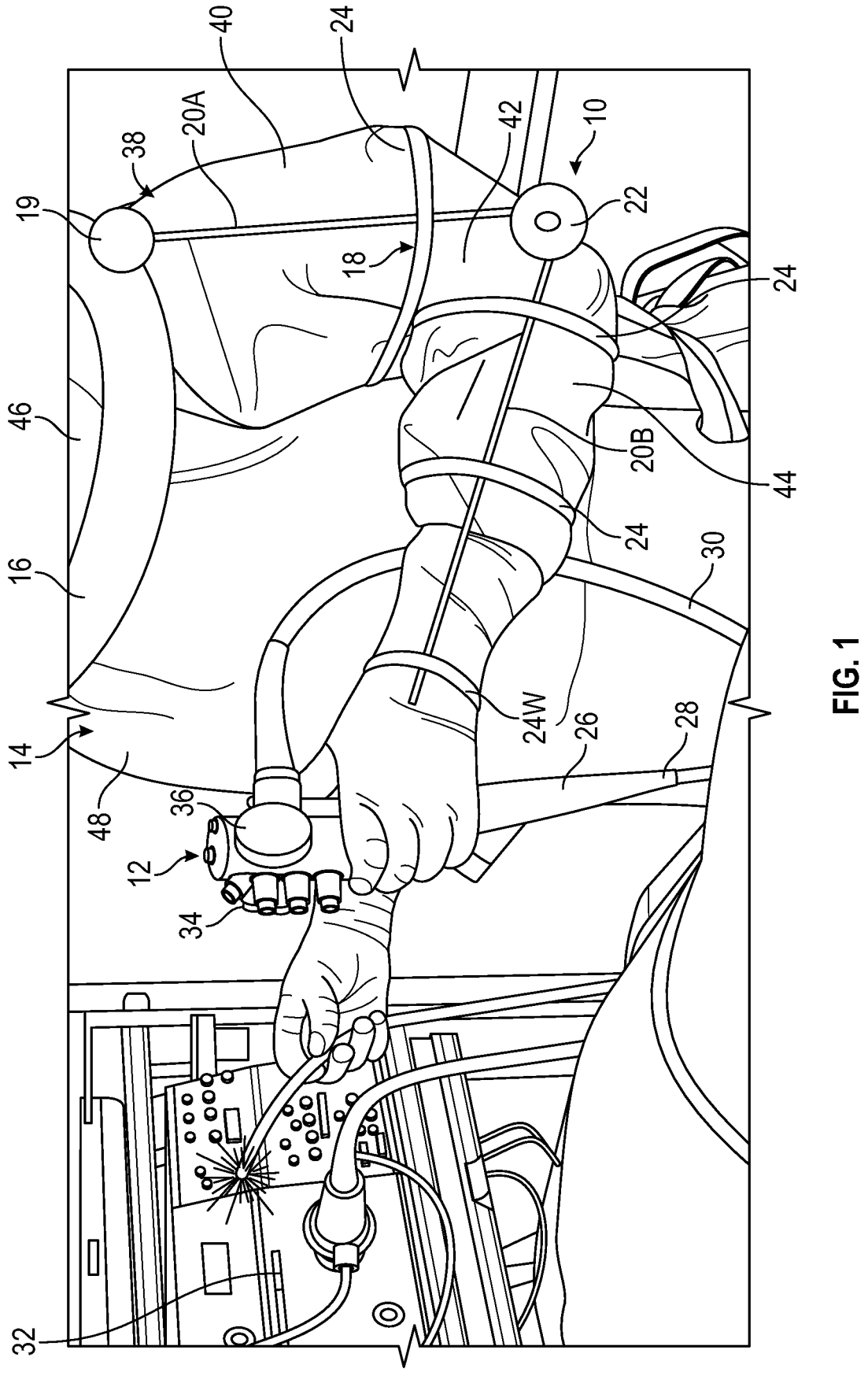
FIG. 1 is a schematic illustration of an exoskeleton sleeve structure for supporting a medical instrument mounted to a user.

FIG. 1 is a schematic illustration of exoskeleton sleeve structure 10 for supporting medical instrument 12 mounted to user 14. Exoskeleton sleeve structure 10 can comprise base 16 and arm 18, which can comprise shoulder joint 19, humeral portion 20A and ulnar portion 20B, elbow joint 22 and shells 24. Medical instrument 12 can comprise handle 26, shaft 28 and control cable 30 that can plug into system 32. Handle 26 can comprise various controllers for operating features of medical instrument 12 and system 32, such as buttons 34 and knob 36. User 14 can comprise arm 38, including bicep 40, elbow 42 and forearm 44, neck area 46 and chest area 48.

User 14 is illustrated administering medical instrument 12 to a patient within an operating room such that shaft 28 can be extended into an opening or incision in the patient. In order to navigate medical instrument 12 to the desired location within the patient and to thereafter operate medical instrument 12, user 14 can manipulate buttons 34 and knob 36. Information, such as video imaging, collected by medical instrument 12 can be displayed at system 32, such as on a video screen. Medical instrument 12 can comprise a scope as discussed herein, such as endoscopes and laparoscopes, as well as other instruments and devices.

Figure 2A:
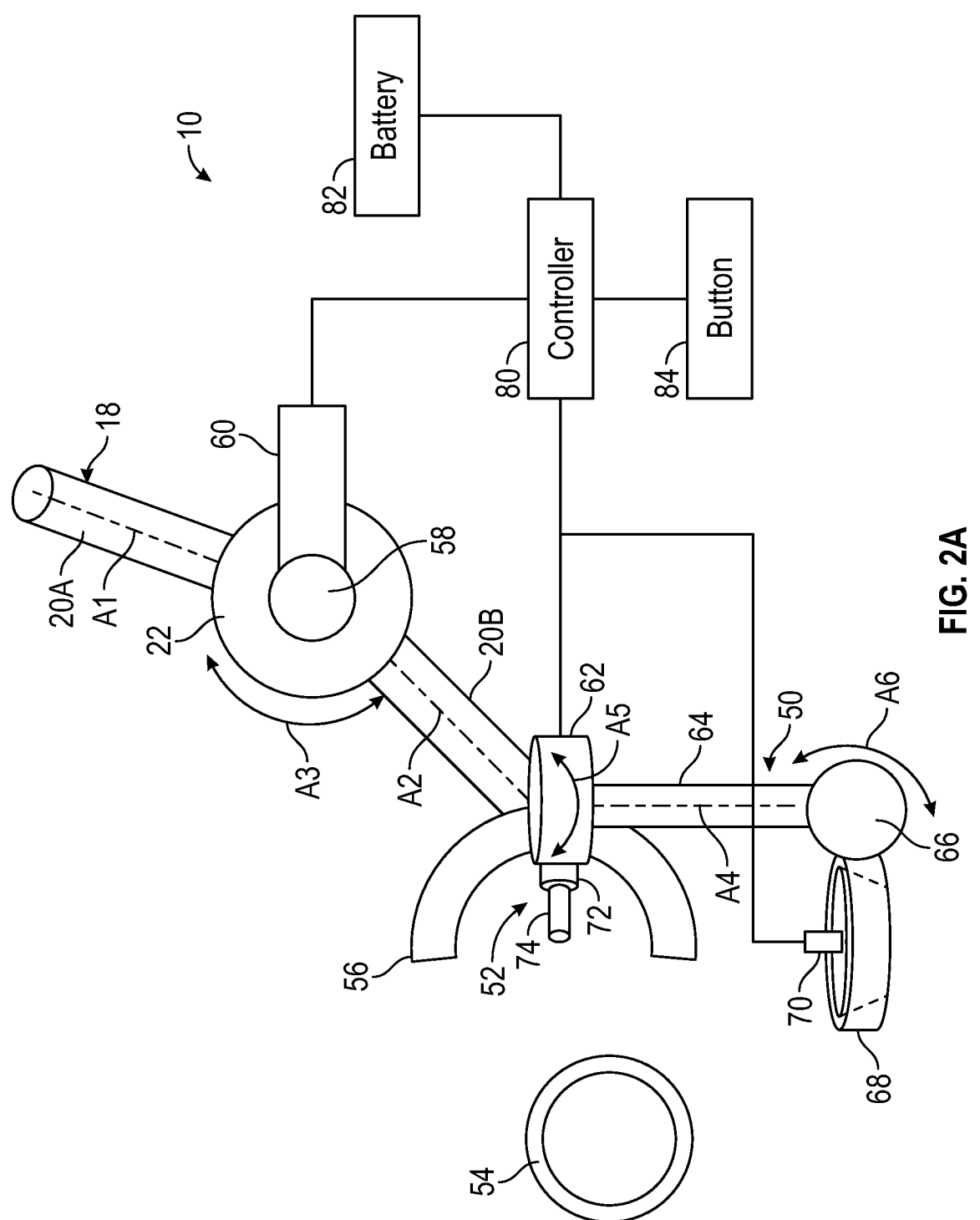
FIG. 2A is a schematic illustration of the exoskeleton sleeve structure of FIG. 1 showing an elbow joint, an instrument holder, an ejector and a retention bracelet.
Figure 2B:
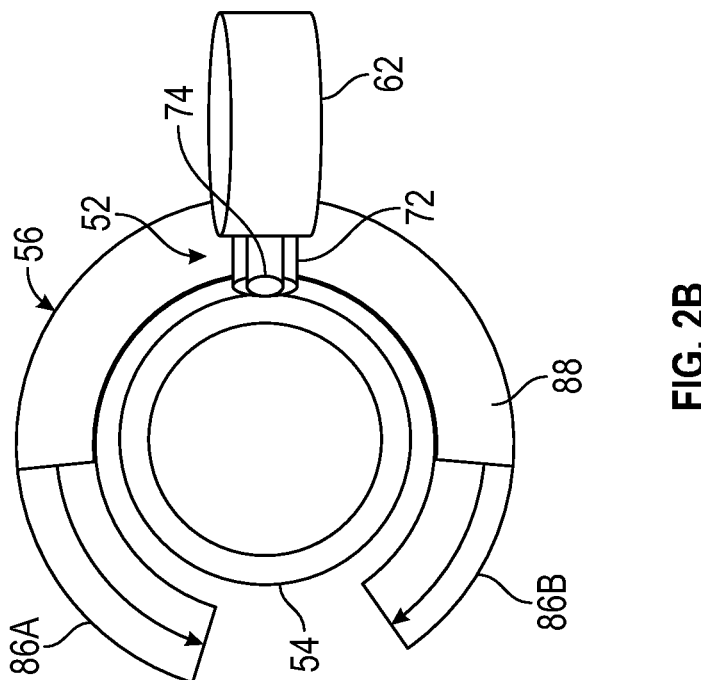
FIG. 2B is a schematic illustration of the exoskeleton sleeve structure of FIG. 2A with the retention bracelet secured in a wrist clasp.

Navigation of medical instrument 12 to the desired location where the target anatomy to be treated is located, and subsequent operation of medical instrument 12 to complete a medical procedure can last varying lengths of time and can sometimes require user 14 to hold medical instrument 12 for a time that can induce fatigue in arm 38. For example, the weight of handle 26, shaft 28 and cable 30 can induce fatigue in bicep 40. Additionally, operation of buttons 34 and knob 36 can induce fatigue in forearm 44. As such, user 14 can utilize structure 10 to provide support to arm 38 while operating medical instrument 12. Structure 10 can comprise an exoskeleton sleeve that fits onto arm 38 to alleviate stress and strain on arm 38. As discussed below, structure 10 can be configured to lock into a user-selected position to allow arm 38 to be easily inserted into and removed from the exoskeleton sleeve to perform other tasks. Additionally, adjustable and powered instrument holders can be attached to structure 10 to allow user-selectable configurations that can further reduce fatigue, as shown in FIGS. 2A and 2B. Furthermore, such adjustable and powered instrument holders and other accessories can be used in conjunction with slings, vests and other garments discussed with reference to FIGS. 6 and 7.

Base 16 can comprise a collar that fits onto neck area 46 of user 14, such as to surround the neck of user 14. The collar can comprise a padded brace that distributes weight to chest area 48. Such collars can fit over the head of the user or can be opened to allow for positioning around the neck. Base 16 can partially or completely surround the neck such that base 16 can rest on one or both shoulders of user 14. In additional examples, base 16 can comprise a freestanding pedestal that can rest on the floor of the operating room near user 14. Such a pedestal can be mounted on wheels to allow structure 10 to follow user 14.

Humeral portion 20 can extend from base 16 at shoulder joint 19. Shoulder joint 19 can comprise a ball joint or universal joint that allows unlimited pivoting and rotation of humeral portion 20A relative to base 16. In examples, shoulder joint 19 can comprise a resistance joint where force from arm 38 can adjust shoulder joint 19, but when force is not applied to shoulder joint 19, shoulder joint 19 will remain in its current or last position. In additional examples, shoulder joint 19 can be locked by a user intervention, such as by contemporaneously being locked with elbow joint 22 when elbow joint 22 is locked as discussed below.

Humeral portion 20A can comprise an elongate body that can support ulnar portion 20B. In example, humeral portion 20A can comprise a rigid rod fabricated from metallic or polymer material. Humeral portion 20A can have a length that is approximately the length of a humeral bone of an average person to extend along bicep 40. In examples, humeral portion 20A can have an adjustable length, such as by having two segments that are slidable relative to each other in a telescoping fashion with one of the segments having a spring-loaded detent that can fit into one of a plurality of seats in the other segment. Humeral portion 20A can comprise a platform for mounting one or more of shells 24. Humeral portion 20A is shown having a single one of shells 24. In examples, humeral portion 20A can include a plurality of shells 24 spaced at regular or irregular intervals to provide attachment to arm 38.

Ulnar portion 20B can be configured similarly as humeral portion 20A except being constructed for being attached to an ulnar bone instead of a humeral bone to extend along forearm 44. Humeral portion 20A and ulnar portion 20B are illustrated as comprising straight, cylindrical rods. However, humeral portion 20A and ulnar portion 20B can be curved or contoured to more comfortably mate with bicep 40 and forearm 44 and can have other cross-sectional profiles. Ulnar portion 20B can include shell 24W that can be particularly suited for coupling to a wrist of arm 38. As discussed below with reference to FIGS. 2A and 2B, shell 24W can be configured to latch onto the wrist so that user 14 can induce pivoting at joints 19 and 22 and pull exoskeleton sleeve structure 10 to desired locations along with arm 38.

Shells 24 can be mounted to humeral portion 20A and ulnar portion 20B in fixed positions or can be mounted on slidable joints that allow for user-customization of the placement of shells 24. Shells 24 can comprise brackets configured to fit over an outer or lateral portion of arm 38. Shells 24 can comprise C-shaped brackets, as illustrated in FIG. 1. In examples, shells 24 can be fabricated of resilient material to allow arm 38 to be pushed into the C-shaped brackets and then allow the resiliency of the material to hold onto arm 38. Shells 24 can comprise one-hundred-eighty-degree circular segments. However, shells 24 can subtend more or less than one-hundred-eighty-degrees and can have other shapes than circular.

Elbow joint 22 can comprise a ball joint or universal joints that allows unlimited pivoting and rotation of ulnar portion 20B relative humeral portion 20A. In examples, elbow joint 22 can comprise a resistance joint where force from arm 38 can adjust elbow joint 22, but when force is not applied to elbow joint 22, elbow joint 22 will remain in its current or last position. In examples, elbow joint 22 can be selectively locked into position by user 14 to additionally support the weight of arm 38 or allow medical instrument 12 to be locked into position relative to the patient, as discussed with reference to FIGS. 2A-3.

The position and shape of structure 10 can allow for arm 38 to be easily inserted into and removed from structure 10. For example, wrist shell 24W can allow structure 10 to be attached to arm 38 so that movement of arm 38 can pull arm 18 to a desired orientation. Thereafter, as discussed below, user 14 can lock arm 18 into place and remove arm 38 from shells 24 after releasing wrist shell 24W. For example, the C-shape, or otherwise open shape of shells 24 in the medial direction, e.g., toward chest area 48, can allow user 14 to pull arm 38 from arm 18. User 14 can thereafter use arm 38 to perform other tasks. Handle 26 can be suspended from or held in place on structure arm 18, as discussed below.

FIG. 2A is a schematic illustration of structure 10 of FIG. 1 showing elbow joint 22, instrument holder 50, ejector 52 and retention bracelet 54. Arm 18 can comprise humeral portion 20A and ulnar portion 20B, elbow joint 22 and wrist clasp 56. Shells 24 (FIG. 1) have been omitted for clarity. Elbow joint 22 can comprise locking device 58 and sensor 60. Instrument holder 50 can comprise horizontal adjuster, 62, extension 64, angle adjuster 66, instrument socket 68 and control element 70. Ejector 52 can comprise base 72 and pusher 74. Structure 10 can be connected to controller 80, which can be connected to sensor 60 and lock 58, ejector 52 and control element 70. Controller 80 can additionally be connected to battery 82 and button 84.

Humeral portion 20A can extend from base 16 (FIG. 1), which is not shown in FIG. 2A for simplicity. Additionally, shells 24 are omitted from humeral portion 20A and ulnar portion 20B in FIG. 2A for clarity. Humeral portion 20A can extend along axis A1 and ulnar portion 20B can extend along axis A2. Elbow joint 22 can allow ulnar portion 20B to pivot relative to humeral portion 20A, as indicated by arrow A3. As discussed, elbow joint 22 can comprise a universal joint. However, in examples, ulnar portion 20B and humeral portion 20A can be constrained to rotate in a single plane. In examples, ulnar portion 20B can rotate about longitudinal axis A2 to allow wrist clasp 56 to rotate with the wrist of user 14. Elbow joint 22 can be operated by controller 80. For example, elbow lock 58 can be automatically activated via sensor 60, either to lock or unlock when the presence of arm 38 is sensed.

Wrist clasp 56, which can comprise wrist shell 24W (FIG. 1), can be provided at the distal end of ulnar portion 20B or in close proximity thereto. Wrist clasp 56 can be configured to secure the wrist of user 14 in one or more ways. In the illustrated example, bracelet 54 can be configured to be releasably attached to arm 18, such as via magnetic force. In additional examples, bracelet 54 can be attached to wrist clasp 56 via hook and loop fastener material. Additionally, as shown in FIG. 2B, clasp 56 can be configured to encircle or partially encircle bracelet 54, such as through the use of retractable extensions 86A and 86B (FIG. 2B) or straps. Bracelet 54 can be fabricated from a ferromagnetic material, such as iron. A portion of arm 18 or a component on arm 18 can be configured to generate a magnetic field to pull bracelet 54 into wrist clasp 56. In examples, base 72 can be magnetized, such as by being fabricated from a magnetized material or by having an electro-magnetic field generated by base 72 via operation from controller 80. Operation of the magnetic field can be coordinated with the operation of other components of structure 10, such as ejector 52 and elbow lock 58.

Ejector 52 can be configured to push arm 38 (FIG. 1) out of arm 18, or assist in user 14 pulling arm 38 out of arm 18. In the illustrated example, pusher 74 can comprise a retractable pin that can be extended to push against arm 38. In other examples, ejector 52 can comprise a pivotable plate that is, for example, hinged to wrist clasp 56 and pushed by pusher 74. Pusher 74 can be configured to extend from base 72 or can comprise a separate component from base 72. Pusher 74 can be electrically activated, pneumatically activated or magnetically activated, or activated by any other suitable means. Ejector 52 can be operated by controller 80.

Instrument holder 50 can extend from ulnar portion 20B. In examples, instrument holder 50 can be connected to ulnar portion 20B via horizontal adjuster 62. Bracket 64 can extend from horizontal adjuster 62 in a superior-inferior direction to position instrument socket 68 below wrist clasp 56. In examples, bracket 64 can be adjustable in length, such as by having telescoping sections. Instrument socket 68 can be connected to bracket 64 via angle adjuster 66. Instrument socket 68 can be configured to hold a distal portion of handle 26 (FIG. 1) while a proximal portion of handle 26 can be located proximate wrist clasp 56 where user 14 can grasp handle 26. In examples, instrument socket 68 can be configured with two or more sockets or receptacles for holding two or more instruments. For example, socket 68 can be configured to hold handles of a duodenoscope and a cholangioscope. Socket 68 can be rotated, for example, into and out of the plane of FIG. 2A, to orient each socket relative to wrist clasp 56. In additional examples, multiple instances of socket 68 can be attached to arm 18. For example, two sockets 68 could be attached to adjuster 66 and bracket 64 can be configured to rotate about axis A4 to position different ones of sockets 68 relative to wrist clasp 56. In examples, different sockets 68 can be located at different levels along bracket 64 to accommodate handles with different lengths.

Horizontal adjuster 62 and angle adjuster 66 can be user-activated components that can be used to set the position of instrument socket 68 and handle 26 (FIG. 1) located therein, relative to wrist clasp 56. Bracket 64 can be rotated about axis A4 as indicated by arrow A5. Thus, instrument support 68 can be rotated into and out of the plane of FIG. 2A. Instrument support 68 can be rotated perpendicular to bracket 64 along an axis extending into the plane of FIG. 1 so as to be moveable up and down in FIG. 2A as shown by arrow A6.

In examples, adjusters 62 and 66 can comprise ratchet mechanisms that can allow positioning into a plurality of discrete positions. For example, adjusters 62 and 66 can comprise concentric joints having opposing detents and seats, respectively. In additional examples, adjusters 62 and 66 can allow for continuous adjustment into an infinite number of positions, i.e., no discrete or pre-determined positions are provided. For example, adjusters 62 and 66 can comprise opposing rings mounted together with a resistance fit. Thus, adjusters 62 and 66 can be configured to hold their position when under minimal loading, such as the weight of instrument 12, but can be adjusted by user 14. In additional examples, adjusters 62 and 66 can be motorized to be actuated by controller 80.

Controller 80 can comprise a device to coordinate operation of the devices of structure 10, such as elbow lock 58, wrist clasp 56, ejector 52, control element 70, button 84 and adjusters 62 and 66. In examples, controller 80 can comprise a microprocessor device connected to button 84. In examples, controller 80 can comprise a separate device, such as a mobile phone or tablet computer or another handheld device, that can be worn by user 14. Button 84 can comprise a user-activated switch that can be used to control one or more features of structure 10. In examples, button 84 can comprise a pedal for positioning on a floor of an operating room. The pedal can comprise a multi-position pedal to control different devices, or combinations of devices, of structure 10. In examples, controller 80 can communicate with button 84, elbow lock 58, sensor 60, ejector 52 and control element 70 via a wireless communication link, such as Bluetooth. In examples, controller 80 can communicate with button 84, elbow lock 58, sensor 60, ejector 52 and control element 70 via a wired connection.

During operation, a wrist of user 14 can be placed in bracelet 54, bracelet 54 can be positioned within wrist clasp 56, and pusher 74 can be retracted into base 72, as shown in FIG. 2B. Arm 38 can be positioned within shells 24 (FIG. 1) and attached thereto as described above. As such, arm 38 (FIG. 1) of user 14 can be moved to pull arm 18 along into a desired position where handle 26 (FIG. 1) is supported by instrument holder 50 in a comfortable position relative to user 14. Elbow lock 58, as well as another lock provided on shoulder joint 19 (FIG. 1), can be activated by automatically activated by sensor 60 or user activated by button 80 to lock arm 18 in place. Ejector 52, wrist clasp 56 and magnetic base 72 can thereafter be activated to allow arm 38 to be freely removed from arm 18 to allow user 14 to separate from structure 10 to perform other tasks without the aid of arm 18. Controller 80 can thus coordinate one or more or all of the devices of structure 10 to facilitate such operation. In examples, user 14 can select which devices are used and how they are activated or deactivated.

FIG. 2B is a schematic illustration of structure 10 of FIG. 2A with retention bracelet 54 secured in wrist clasp 56. Pusher 74 can be retracted into base 72 and bracelet 54 can be brought into contact with base 72. Additionally, wrist clasp 56 can comprise wraps 86A and 86B that can extend from base 88 to surround or partially surround a wrist of user 14 (FIG. 1).

FIG. 2B illustrates a configuration where arm 38 (FIG. 1) is positioned within arm 18 (FIG. 2A). Presence sensor 60 (FIG. 2A) can sense the position of arm 38 against elbow joint 22. If arm 38 is sensed. Controller 80 (FIG. 1) can operate to do one or more of 1) release elbow lock 58 to enable humeral portion 20A and ulnar portion 20B to move relative to each other as indicated by arrow A1, 2) generate a magnetic field generated with base 72 to attract bracelet 54, 3) retract pusher 74 and 4) deploy extensions 86A and 86B. Furthermore, floor button 84 can be used to perform any one or more of items 1)-4). Additionally, button 84 can be configured to by user 14 to override one or more of items 1)-4), such as to allow removal of arm 38 form arm 18.

Thus, with items 1)-4) being performed, user 14 can move arm 38 to move structure 10 into a position relative to user 14 where it is comfortable to use medical instrument 12 and adjust adjusters 62 and 66 to move medical instrument 12 to where it is comfortable relative to wrist clasp 56 and the hand of user 14. The hand of user 14 can be retained against arm 18 of structure 10 via wrist clasp 56. When user 14 wants to rest arm 38, floor button 84 can be activated to activate elbow lock 58, thus relieving arm 38 of having to support medical instrument 12. When user 14 is ready to preform a task not involving medical instrument 12 with arm 18, user 14 can activate floor button 84 to release bracelet 54, thereby allowing user 14 to remove arm 38 from structure 10 while structure 10 supports medical instrument 12 in a position for activate elbow lock 58. Further, activation of button 84 can additionally activate ejector 52 to push arm 38 out of arm 18. Force of ejector 52 can, for example, be used to overcome magnetic attraction between bracelet 54 and base 72 or hook and loop fastener material of extensions 86A and 86B.

Figure 3:
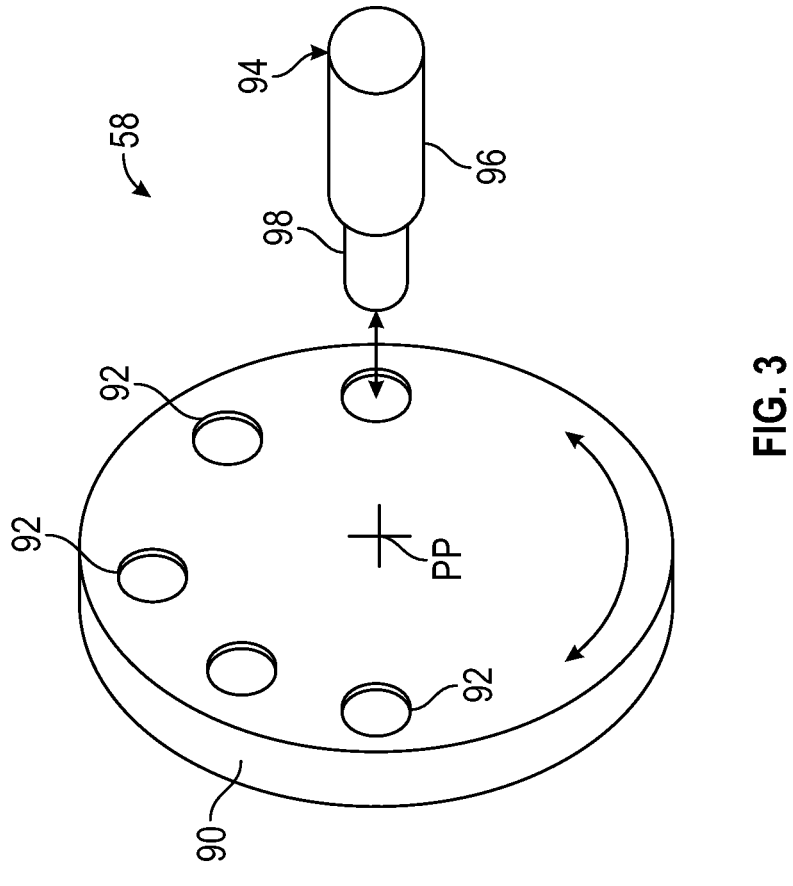
FIG. 3 is a schematic perspective view of a locking device for the elbow joint of FIG. 2A.

FIG. 3 is a schematic perspective view of locking device 58 for elbow joint 22 of FIG. 2A. Locking device 58 can comprise plate 90, which can have sockets 92, and actuator 94, which can comprise base 96 and pin 98. Actuator 94 can be configured to engage plate 90, such as via operation by controller 80, to prevent relative movement therebetween.

Figure 4:
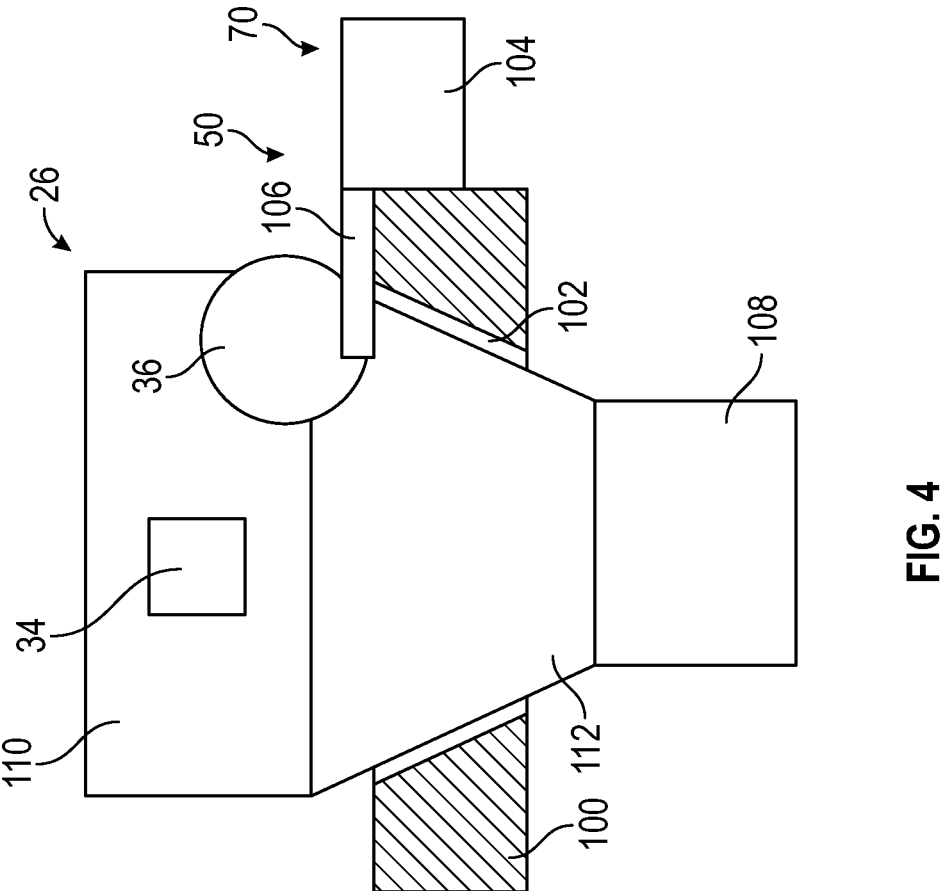
FIG. 4 is a schematic cross-sectional view of the instrument holder of FIG. 2A showing an instrument handle engaging a control element.

In examples, plate 90 can be mounted to humeral portion 20A and actuator 94 can be mounted to ulnar portion 20B. Sockets 92 can be arranged along an arcuate path on plate 90 centered about pivot point PP between humeral portion 20A and ulnar portion 20B. As ulnar portion 20B is moved relative to humeral portion 20A, actuator 94 can be moved along the arc of sockets 92. When actuator 94 is activated, or deactivated, pin 98 can protrude from base 96 to extend into one of sockets 92, thereby preventing movement between humeral portion 20A and ulnar portion 20B. Actuator 94 can comprise a solenoid or another electrically activated switch, operated by controller 80. In examples, actuator 94 can be electrically activated, e.g., caused to protrude and retract by active electrical signal. In other examples, pin 98 can be biased, such as via one or more springs, into a protruded or retracted position and electrically activated to overcome the spring force. In examples, locking device 58 can be employed in shoulder joint 19 (FIG. 1). FIG. 3 illustrates one example of a locking device suitable for use in joints 19 and 22. In additional examples, FIG. 4 is a schematic cross-sectional view of instrument holder 50 of FIG. 2A showing instrument handle 26 engaging control element 70. Instrument holder 50 can comprise cup 100 having socket 102. Control element 70 can comprise actuator 104 and detent 106. Handle 26 can comprise inferior portion 108, superior portion 110 and tapered portion 112. Inferior portion 108 can connect to shaft 28 (FIG. 1). Superior portion 110 can include controllers, such as button 34 and wheel 36. Tapered portion 112 can be configured to fit within socket 102.

Cup 100 can be located in or connected to instrument support 68 of FIG. 2A. Socket 102 can be shaped to conform with handle 26. In the illustrated example, socket 102 can be angled or funnel-shaped to mate with tapered portion 112 of handle 26. Mating of tapered portion 112 with socket 102 can prevent handle 26 from passing through cup 100.

Figure 5:
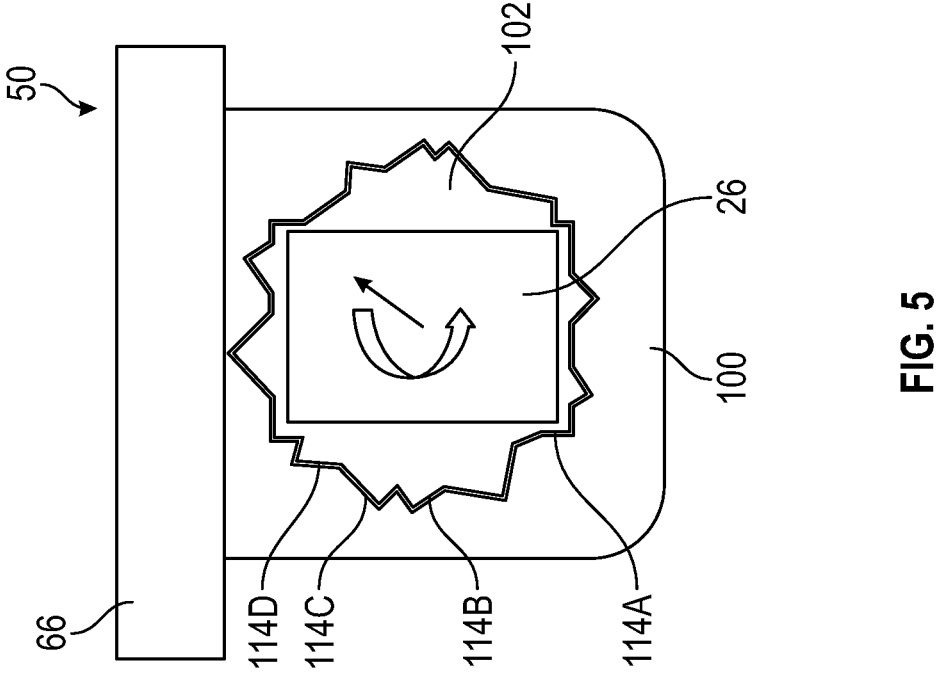
FIG. 5 is a schematic top view of the instrument holder of FIG. 2A showing an instrument handle engaged with a socket having a plurality of discrete positions for the handle.

Distal portion 108 can extend through instrument support 68 so as to be located underneath cup 100, thereby allowing shaft 28 (FIG. 1) to reach the patient without interference. In examples, cup 100 can form a complete ring or loop that encircles handle 26, as can be seen in FIG. 5. In such examples, shaft 28 can be fed through cup 100 before engagement with handle 26. However, in other examples, cup 100 can form a partial ring or loop to allow handle 26 to be inserted laterally in and out of instrument support 68. In additional examples, cup 100 can be selectively opened and closed to allow for passage of handle 26 without having to feed shaft 28 first.

Proximal portion 110 can be located above cup 100 to allow user 14 to access button 34 and knob 36. Cup 100 and socket 102 can be configured to hold handle 26 so that one or both of button 34 and knob 36 can engage control element 70. In examples, control element 70 can comprise a fixed feature to depress button 34 or hold knob 36 in position, thereby alleviating user 14 from having to perform such as task. In examples, control element 70 can be a selectively actuatable feature to depress button 34 on demand or adjust the position of knob 36 on demand, thereby relieving user 14 from having to exert energy to do so. Thus, actuator 104 can be configured to selectively extend and retract detent 106, such as by operation of a button or the like at controller 80 (FIG. 1) or button 84.

FIG. 5 is a schematic top view of instrument holder 50 of FIG. 2A showing instrument handle 26 engaged with socket 102 having a plurality of discrete positions 114A-114D for handle 26. Instrument holder 50 can be connected to arm 18 via angle adjuster 66. Angle adjuster 66 be rotated to adjust the angle of instrument holder 50 into and out of the plane of FIG. 5. Cup 100 can include socket 102, which, in the configuration of FIG. 5, can comprise positions 114A-114D. Positions 114A-114D can comprise surfaces or facets of socket 102 that can cooperate to hold handle 26 in different positions in the plane of FIG. 5. Cup 100 can be fabricated from a rigid material so as to resist rotation of handle 26. Thus, handle 26 can be fixed in different rotational positions relative to the plane of FIG. 5. Positions 114A-114D can be provided and used alternatively to adjuster 62 or complimentary with adjuster 62.

Figure 6:
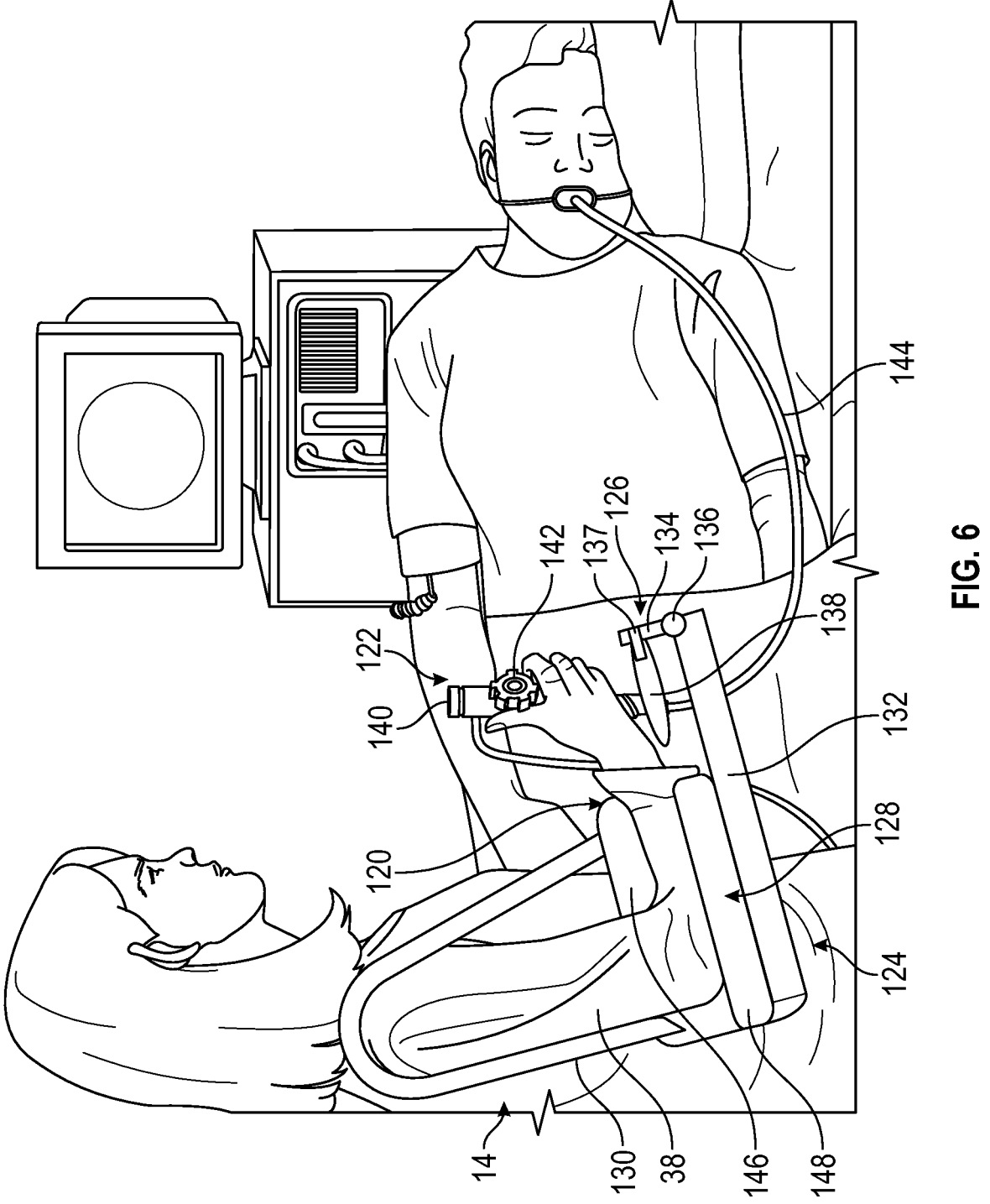
FIG. 6 is a schematic illustration of a structure for supporting a medical instrument relative to a user comprising a sling having an adjustable instrument holder.

FIG. 6 is a schematic illustration of structure 120 for supporting medical instrument 122 comprising sling 124 having instrument holder 126. Sling 124 can comprise pouch 128 and strap 130. Instrument holder 126 can comprise extension 132, bracket 134, joint 136, joint 137 and cup 138. Instrument 122 can comprise handle 140, control knob 142 and shaft 144, and can be configured similarly as instrument 12 of FIG. 1.

Sling 124 can be positioned over a shoulder or neck of user 14 to suspend pouch 128 therefrom. Strap 130 can comprise a flexible strap or belt configured to suspend pouch 128 from user 14. Strap 130 can be adjustable in length so as to allow user 14 to position pouch 128 at a comfortable level. Sling 124 can distribute the load of pouch 128, e.g., the weigh of arm 128, to other portions of the body of user 14. As such, muscles of arm 38 can be relaxed to reduce fatigue on user 14. In examples, strap 130 can be replaced by a garment, such as a vest, that is connected to pouch 128. In examples, the garment attached to pouch 128 can be similar to garment 158 of FIG. 7.

Pouch 128 can comprise a compartment or container to hold forearm of arm 38 of user 14. Pouch 128 can comprise medial wall 146 and lateral wall 148, with medial wall 146 being configured to be against user 14 and lateral wall 148 being configured to face away from user 14. Pouch 128 can be open at a superior and anterior portions to allow bicep and wrist of arm 38 to extend therefrom. Accordingly, inferior and posterior portions of pouch 128, as well as medial and lateral sides, can be closed to hold arm 38. Furthermore, lateral wall 148 can be configured to fold down, as schematically shown in FIG. 6, to allow user 14 to remove arm 38 from pouch 128. In such examples, strap 130 can be connected to portions of pouch 128 not including lateral wall 148. In other examples lateral wall 148 can comprise a partial wall over which arm 38 can be lifted without interference from strap 130. As such, user 14 can remove arm 38 from pouch 128 while sling 124 still supports instrument 122.

In examples, sling 124 can be configured similarly to the devices described in U.S. Pat. No. 2,875,754 titled "Surgical Sling;" U.S. Pat. No. 4,220,149 titled "Arm Sling;" and U.S. Pat. No. 2,594,809 titled "Arm Sling," each of which is incorporated by reference in its entirety. Such slings can be modified to include a lateral wall that is foldable or reduced in height as described herein and that can be connected to instrument holder 126, as discussed below.

Instrument holder 126 can be attached to sling 124 to hold medical instrument 122 in position relative to arm 38 of user 14. Thus, muscles of arm 38 and the hand of user 14 can be relaxed to reduce fatigue on user 14. Extension 132 can extend from pouch 128 and can comprise a rigid beam or support member. Extension 132 can extend along the length of pouch 128 to both support arm 38 and support cup 138. Extension 132 can be fixed relative to pouch 128 or can be configured to slide along pouch 128 or have an adjustable length to allow the distance that cup 138 extends from pouch 128 to be adjusted. Cup 138 can be configured similarly as cup 100 of FIGS. 4 and 5. Cup 138 can be configured to receive handle 140 of instrument 122. As discussed with reference to FIG. 5, cup 138 can allow handle 140 to be fixed in different rotational positions. Additionally, or alternatively, cup 138 can be pivotably connected to bracket 134 via joint 137 to allow rotation into and out of the plane of FIG. 6. Joint 136 can additionally be used to adjust the angle between cup 138 and extension 132 to allow for adjustability of the angular position of medical instrument 122 within the plane of FIG. 6. Cup 138 can additionally be provided with a control element similar to control element 70 (FIG. 4).

Figure 7:
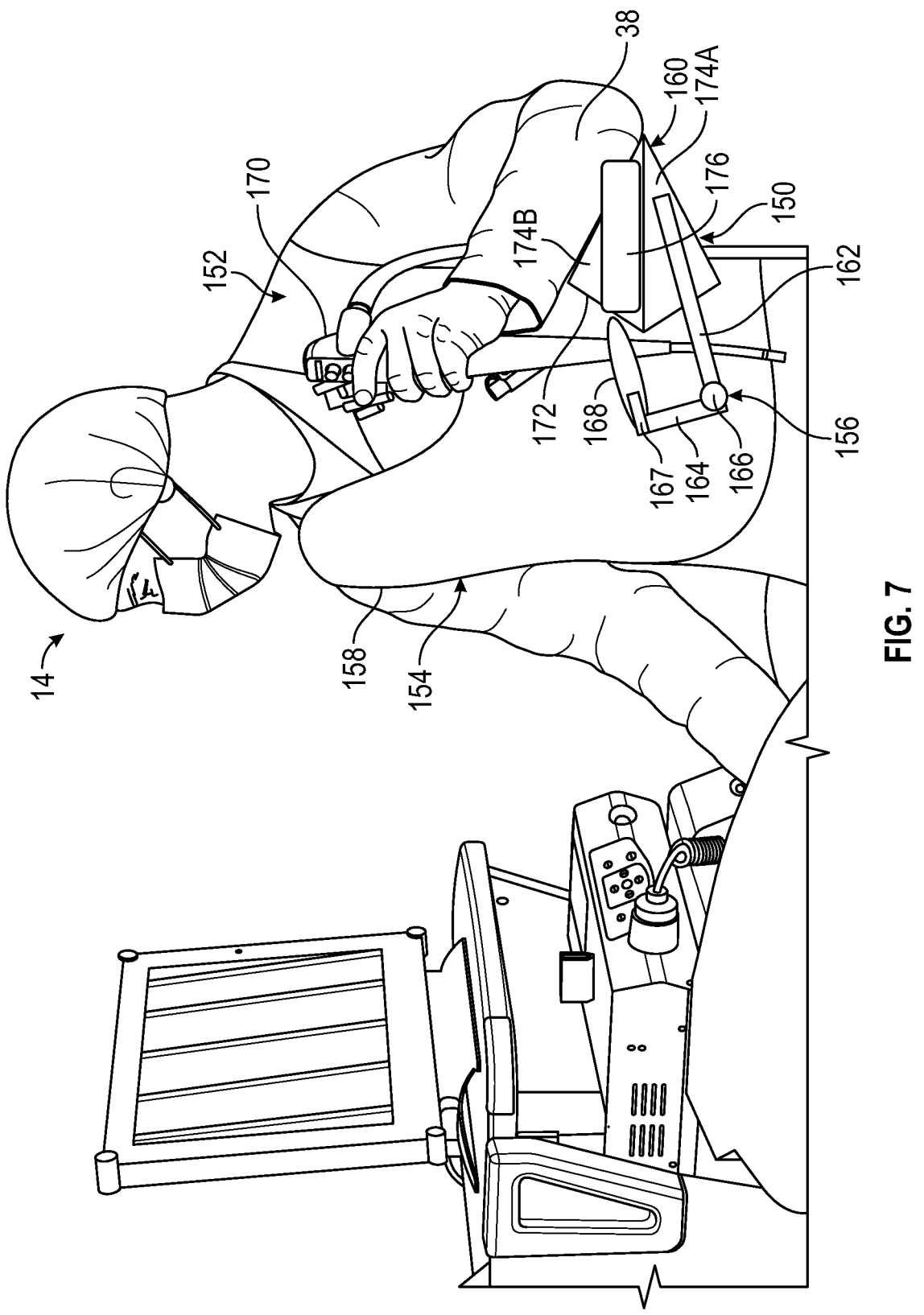
FIG. 7 is a schematic illustration of a structure for supporting a medical instrument relative to a user comprising a vest having an adjustable instrument holder.

FIG. 7 is a schematic illustration of structure 150 for supporting medical instrument 152 comprising vest 154 having instrument holder 156. Vest 154 can comprise garment 158 and pillow 160. Instrument holder 156 can comprise extension 162, bracket 164, joint 166, joint 167 and cup 168. Instrument 152 can comprise handle 170 and can be configured similarly as instrument 12 of FIG. 1.

Garment 158 can be positioned over the chest area of user 14. Garment 158 can be made of fabric or a pliable material to allow a comfortable fit on user 14. Garment 158 can be strong enough to support pillow 160. Garment 158 can be attached in a releasable manner to pillow 160. Garment 158 can include specific locations where pillow 160 can be attached or pillow 160 can be configured to be attached to any location on garment 158. Pillow 160 can be attached to garment 158 in a fixed position, such as via stitching or the use of fasteners, or in adjustable positions, such as via hook and loop fastener material, buttons or zippers. In examples, garment 158 can be replaced with a strap or belt having ends attached to pillow 160. In examples, the strap attached to pillow 160 can be similar to strap 130 of FIG. 6.

Pillow 160 can be rigid enough to support arm 38 of user 14. Pillow 160 can, however, be soft and compliant to conform to arm 38 for the comfort of user 14. In examples, pillow 160 can be made of foam. However, pillow 160 can comprise a rigid body to simply provide a platform or shelf for arm 38. Pillow 160 can comprise a structure having a plurality of different facets or surfaces that can be attached to garment 158. The surfaces can be of different shapes and sizes. In the illustrated example, pillow 160 comprises a pyramid having base 172 and facets 174A and 174B. A user can select which surface is most comfortable or most supportive for arm 38 to face up and can position base 172 against garment 158 in a location suitable for user 14.

In examples, vest 154 can be provided with features that can hold arm 38 onto pillow 160. For example, the sleeve of a lab coat of user 14 can be provided with hook and loop fastener material to mate with hook and loop fastener material on pillow 160. Additionally, pillow 160 can comprise straps to loop over the forearm of user 14. In examples, facets 174A and 174B can be contoured to seat the forearm into pillow 160 to make removal of arm 38 more difficult. Also, pillow 160 can be provided with foldable lateral wall 176 or barrier that can keep arm 38 sandwiched between user 14 and lateral wall 176 to prevent arm 38 from leaving pillow 160. In the various examples, vest 154 can be configured to allow arm 38 to be supported when user 14 desires, but can allow user 14 to remove arm 38 for other purposes while instrument holder 156 continues to support instrument 152.

Instrument holder 156 can be attached to pillow 160 to hold medical instrument 152 in position relative to arm 38 of user 14. Thus, muscles of arm 38 and the hand of user 14 can be relaxed to reduce fatigue on user 14. Extension 162 can extend from pillow 160 and can comprise a rigid beam or support member. Extension 162 can extend along the length of pillow 160 to both support arm 38 and support cup 168. Extension 162 can be fixed relative to pillow 160 or can be configured to slide along pillow 160 or have an adjustable length to allow the distance that cup 168 extends from pillow 160 to be adjusted. Cup 168 can be configured similarly as cup 100 of FIGS. 4 and 5. Cup 168 can be configured to receive handle 170 of instrument 152. As discussed with reference to FIG. 5, cup 168 can allow handle 170 to be fixed in different rotational positions. Additionally, or alternatively, cup 168 can be pivotably connected to bracket 164 via joint 167 to allow rotation into and out of the plane of FIG. 7. Joint 166 can additionally be used to adjust the angle between cup 168 and extension 162 to allow for adjustability of the angular position of medical instrument 170 within the plane of FIG. 7. Cup 168 can additionally be provided with a control element similar to control element 70 (FIG. 4).

VARIOUS NOTES & EXAMPLES

Example 1 is a system for supporting a surgical instrument relative to a body of a user, the system comprising: a body-mountable portion for supporting an arm of the user, the body-mountable portion comprising a forearm support; an instrument support connected to the body-mountable portion to hold a handle of the surgical instrument proximate the forearm support; and a positioning device configured to hold a position of the instrument support relative to the body-mountable portion.

In Example 2, the subject matter of Example 1 optionally includes the body-mountable portion comprising a sling comprising: a pouch defining the forearm support, the pouch including a foldable lateral wall; and a strap connected to the pouch to extend over a shoulder of the user.

In Example 3, the subject matter of any one or more of Examples 1-2 optionally includes a body-mountable portion comprising a vest configured to attach to a chest of the user.

In Example 4, the subject matter of any one or more of Examples 1-3 optionally includes a body-mountable portion comprises a platform for supporting a forearm of the user.

In Example 5, the subject matter of Example 4 optionally includes a platform comprising a pillow including a lateral barrier.

In Example 6, the subject matter of any one or more of Examples 1-5 optionally includes a body-mountable portion comprising an exoskeleton sleeve.

In Example 7, the subject matter of Example 6 optionally includes an exoskeleton sleeve that is configured to engage an outer side of the arm of the user.

In Example 8, the subject matter of any one or more of Examples 6-7 optionally includes and exoskeleton sleeve comprising: a rigid humeral member; a rigid ulnar member defining the forearm support; and an adjustable joint connecting the humeral member and the ulnar member, the adjustable joint comprising the positioning device.

In Example 9, the subject matter of Example 8 optionally includes an adjustable joint comprising: a plate with a plurality of sockets disposed therein; a pin configured to seat within one of the plurality of sockets; and an actuator to advance and retreat the pin relative to the plate.

In Example 10, the subject matter of any one or more of Examples 1-9 optionally includes a positioning device comprising a ratchet mechanism configured to lock the handle into one of a plurality of different angular positions relative to the forearm support.

In Example 11, the subject matter of any one or more of Examples 1-10 optionally includes a positioning device that is adjustable in the medial-lateral direction.

In Example 12, the subject matter of any one or more of Examples 1-11 optionally includes a positioning device that is adjustable in the superior-inferior direction.

In Example 13, the subject matter of any one or more of Examples 1-12 optionally includes a positioning device comprising a socket configured to receive the handle of the instrument in a plurality of discrete positions.

In Example 14, the subject matter of any one or more of Examples 12-13 optionally includes a socket comprising a detent configured to hold a control element of the handle in a fixed position.

In Example 15, the subject matter of any one or more of Examples 12-14 optionally includes a socket comprising an actuator configured to selectively operate a control element of the handle.

In Example 16, the subject matter of any one or more of Examples 1-15 optionally includes a foot pedal to control operation of the positioning device.

In Example 17, the subject matter of any one or more of Examples 1-16 optionally includes a wireless communication device configured to communicate with the positioning device.

In Example 18, the subject matter of any one or more of Examples 1-17 optionally includes an ejector configured to push the arm of the user out of the forearm support.

In Example 19, the subject matter of any one or more of Examples 1-18 optionally includes a bracelet for wearing by the user; and a magnet for attracting the bracelet to the forearm support.

In Example 20, the subject matter of any one or more of Examples 1-19 optionally includes a forearm support comprising an adjustable clasp.

Example 21 is a structure for supporting a medical instrument for a user, the structure comprising: a support base defining a stationary structure; an exoskeleton connected to the support base, the exoskeleton comprising: a humeral support extending form the support base; an elbow pivot joint connected to the humeral support; and an ulnar support extending from the elbow pivot joint; a locking mechanism for the elbow pivot joint; and a device support connected to the ulnar support.

In Example 22, the subject matter of Example 21 optionally includes a support base comprising a collar for positioning about a head of the user or a floor-standing pedestal.

In Example 23, the subject matter of any one or more of Examples 21-22 optionally includes a locking mechanism comprising: a plate with a plurality of sockets disposed therein; a pin configured to seat within one of the plurality of sockets; and an actuator to advance and retreat the pin relative to the plate.

In Example 24, the subject matter of any one or more of Examples 21-23 optionally includes a foot pedal to actuate the locking mechanism.

In Example 25, the subject matter of Example 24 optionally includes an ejector connected to the ulnar support, the ejector configured to push an arm of the user out of the exoskeleton.

In Example 26, the subject matter of Example 25 optionally includes a wireless communication device for communicating control signals with the locking mechanism and the ejector based on operation of the foot pedal.

In Example 27, the subject matter of any one or more of Examples 21-26 optionally includes an exoskeleton comprising a shell configured to be positioned over an outer portion of an arm of the user, the shell comprising a plurality of C-shaped brackets mounted to each of the humeral and ulnar support members.

In Example 28, the subject matter of any one or more of Examples 21-27 optionally includes a device support comprising a ratchet mechanism configured to lock the handle into one of a plurality of different angular positions relative to the ulnar support.

In Example 29, the subject matter of any one or more of Examples 21-28 optionally includes a device support comprising a socket configured to receive a handle of the instrument in a plurality of discrete positions.

In Example 30, the subject matter of any one or more of Examples 21-29 optionally includes a bracelet for wearing by the user; and a magnet for attracting the bracelet to the exoskeleton.

Example 31 is a method for supporting a medical instrument against the body of a user, the method comprising: placing an arm of the user in a support structure; attaching the support structure to the body; positioning the medical instrument in an instrument support connected to the support structure; and adjusting a positioning device to fix a position of the medical instrument relative to the body.

In Example 32, the subject matter of Example 31 optionally includes placing an arm of the user in a support structure by placing a sleeve shell over an outer portion of the arm of the user.

In Example 33, the subject matter of any one or more of Examples 31-32 optionally includes attaching the support structure to the body by positioning a collar around a neck of the user.

In Example 34, the subject matter of any one or more of Examples 31-33 optionally includes positioning the medical instrument in an instrument support connected to the support structure by placing a handle of the medical instrument in a socket comprising a plurality of discrete positions for holding the handle.

In Example 35, the subject matter of any one or more of Examples 31-34 optionally includes positioning the medical instrument in an instrument support connected to the support structure by adjusting a control element of a handle of the medical instrument.

In Example 36, the subject matter of any one or more of Examples 31-35 optionally includes adjusting a positioning device to fix a position of the medical instrument relative to the body by locking a handle into one of a plurality of different angular positions relative to the support structure.

In Example 37, the subject matter of any one or more of Examples 31-36 optionally includes operating a foot pedal to activate the positioning device.

In Example 38, the subject matter of Example 37 optionally includes operating an ejector to push the arm of the user out of the support structure.

In Example 39, the subject matter of Example 38 optionally includes wirelessly communicating between the ejector and the positioning device using the foot pedal.

In Example 40, the subject matter of any one or more of Examples 31-39 optionally includes magnetically attracting a bracelet positioned on an arm of the user to the support structure.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system for supporting an endoscope relative to a body of a user, the system comprising:
   a body-mountable portion for supporting an arm of the user, the body-mountable portion comprising a forearm support;
   an instrument support connected to the body-mountable portion to hold a handle of the endoscope proximate the forearm support; and
   a positioning device configured to hold a position of the instrument support relative to the body-mountable portion;
   wherein the instrument support includes a cup into which a lower portion of the handle is inserted and fixed, the cup having a socket that allows a position for inserting the handle to be selected;
   wherein the positioning device is adjustable in the superior-inferior direction; and
   wherein the cup comprises a control element configured to engage a control element of the handle to control a capability of the endoscope.

2. The system of claim 1, wherein the body-mountable portion comprises a sling comprising:
   a pouch defining the forearm support, the pouch including a foldable lateral wall; and a strap connected to the pouch to extend over a shoulder of the user.

3. The system of claim 1, wherein the body-mountable portion comprises a vest configured to attach to a chest of the user.

4. The system of claim 1, wherein the body-mountable portion comprises a platform for supporting a forearm of the user.

5. The system of claim 4, wherein the platform comprises a pillow including a lateral barrier.

6. The system of claim 1, wherein the body-mountable portion comprises an exoskeleton sleeve.

7. The system of claim 6, wherein the exoskeleton sleeve is configured to engage an outer side of the arm of the user.

8. The system of claim 6, wherein the exoskeleton sleeve comprises:
   a rigid humeral member;
   a rigid ulnar member defining the forearm support; and
   an adjustable joint connecting the humeral member and the ulnar member, the adjustable joint comprising the positioning device.

9. The system of claim 8, wherein the adjustable joint comprises:
   a plate with a plurality of sockets disposed therein, wherein the socket is one of the plurality of sockets;
   a pin configured to seat within one of the plurality of sockets; and
   an actuator to advance and retreat the pin relative to the plate.

10. The system of claim 1, wherein the positioning device comprises a ratchet mechanism configured to lock the handle into one of a plurality of different angular positions relative to the forearm support.

11. The system of claim 1, wherein the positioning device is adjustable in the medial-lateral direction.

12. The system of claim 1, wherein the socket is configured to receive the handle of the endoscope in a plurality of discrete positions.

13. The system of claim 12, wherein the socket comprises a plurality of surfaces configured to cooperate to hold the handle in different rotational positions relative to an axis of the handle within a plane defined by the socket.

14. The system of claim 1, further comprising a foot pedal to control operation of the positioning device.

15. The system of claim 1, further comprising a wireless communication device configured to communicate with the positioning device.

16. The system of claim 1, further comprising an ejector configured to push the arm of the user out of the forearm support.

17. The system of claim 1, further comprising:
   a bracelet for wearing by the user; and
   a magnet for attracting the bracelet to the forearm support.

18. The system of claim 1, wherein the forearm support comprises an adjustable clasp.

* * * * *